United States Patent [19]

O'Connor

[11] Patent Number: 4,578,066

[45] Date of Patent: Mar. 25, 1986

[54] INCONTINENT GARMENT, CATAMENIAL DEVICE OR WOUND DRESSING

[75] Inventor: James J. O'Connor, Calumet County, Wis.

[73] Assignee: Kimberly-Clark Corporation, Neenah, Wis.

[21] Appl. No.: 614,583

[22] Filed: May 29, 1984

[51] Int. Cl.⁴ ............................................. A61F 13/16
[52] U.S. Cl. ..................................... 604/366; 604/378
[58] Field of Search ............... 604/367, 369, 370, 366, 604/374, 378, 379, 380, 381

[56] References Cited

U.S. PATENT DOCUMENTS

| 2,897,109 | 7/1959 | Voigtman . | |
|---|---|---|---|
| 3,230,955 | 1/1966 | Joa et al. . | |
| 3,692,618 | 9/1972 | Dorschner . | |
| 3,886,942 | 6/1975 | Bernardin . | |
| 3,955,577 | 5/1976 | Gellert et al. | 604/366 |
| 4,067,336 | 1/1978 | Johnson . | |
| 4,069,821 | 1/1978 | Fitzgerald et al. | 604/366 |
| 4,219,024 | 8/1980 | Patience et al. | 604/366 |
| 4,505,705 | 3/1985 | Matthews et al. | 604/366 |

Primary Examiner—John D. Yasko
Attorney, Agent, or Firm—Paul A. Leipold; Donald L. Traut; J. J. Duggan

[57] ABSTRACT

The invention relates to a pad that has as the outer impervious layer a polymer sheet integrally bonded to a fabric material such that the fabric material is on the exterior of the polymer sheet. The fabric is exposed on the body side of the pad when the edges of the pad are wrapped with the impervious liner to form baffles. The absorbent material forming the inner portion of the pad is integrally connected to a pervious body-side liner material. The connection of pervious liner to absorbent is such that when the pad is manipulated the pervious liner material stays in contact with the absorbent material and aids in transfer of liquid through the pervious liner into the absorbent. The fabric forming part of the impervious layer is preferably hydrophobic.

13 Claims, 8 Drawing Figures

INCONTINENT GARMET, CATAMENIAL DEVICE OR WOUND DRESSING

LEGAL FIELD

The invention relates to absorbent pads and more particularly to disposable absorbent pads which are suitable for use as incontinence, catamenial or wound dressing devices.

BACKGROUND OF THE INVENTION

It has been generally known in the art to provide disposable absorbent pads. These pads generally are composed of an impervious backing material, absorbent inner structure, and a permeable body-side liner. Pads with this construction have been used as diapers, dressings, feminine pads, or incontinent devices.

An incontinent device such as disclosed in U.S. Pat. No. 4,182,334—Johnson, and a device such as disclosed in U.S. Pat. No. 4,315,508—Bolick, has found acceptance in the incontinent care market. These devices as commercialized have been formed with the impervious outer liner folded over to form baffles at the long edges of the sides of the pad. By folding over the impervious layer to form the baffles, leakage is less likely to occur when the pad is compressed by movement of the wearer. The side baffles are believed to cause the liquid to flow within the pad rather than flowing over the edge. However, the folded-over impervious polymer member forming the baffle may be uncomfortable to the wearer and it has been necessary to cover this baffle with a permeable fabric sheet. However, in covering it with a sheet there has been a tendency for liquids to wick along the covering sheet and wet the clothes of the wearer. Further, the wrapping of the entire pad which is necessary in forming this outer covering has added to expense.

Another difficulty with prior incontinent pads is that the pervious inner liner, if it is not in contact with the absorbent material when liquid is applied to the pad such as by urination, may not immediately transfer the urine through the pad and the urine may run along the surface of the pad and over the edge to wet the clothing of the wearer. Therefore, there is a need for a pad that is less likely to leak by urine running along the liner or by wicking, and further there is a need for a pad that is lower in cost.

DISCLOSURE OF THE INVENTION

It is an object of the invention to form a lower-cost absorbent pad.

Another object of the invention is to form an absorbent pad with less leakage from the sides.

An additional object of the invention is to form an absorbent pad that may be manufactured by simple manufacturing processes.

These and other objects of the invention are generally accomplished by providing a pad that has as the outer impervious layer a polymer sheet integrally bonded to a fabric material. The fabric material is on the exterior of the polymer sheet when forming the outer cover of the pad. The fabric of the outer sheet is exposed to the body side when the edges of the absorbent inner material are wrapped with the impervious liner to form baffles. The absorbent material forming the inner portion of the pad is integratively connected to a pervious body-side liner material to form an integral unit. This connection is such that when the pad is manipulated the pervious liner material stays in contact with the absorbent material and aids in transfer of liquid through the pervious liner into the absorbent.

In a particularly preferred form of the invention, the absorbent material is a coform material. Coform as used herein is defined as a blend of meltblown fibers and cellulose fibers that is formed by air forming a meltblown polymer material while simultaneously blowing air-suspended cellulose fibers into the stream of meltblown fibers. The meltblown fibers containing wood fibers are collected on a foraminous belt that has placed onto its surface a pervious material such as spunbonded fabric material. This spunbonded fabric material serves as a forming base and then in the pad serves as a pervious body-side liner. It is also preferred that the fabric material of the outer layer be hydrophobic.

MODES OF CARRYING OUT THE INVENTION

The instant invention has numerous advantages over prior art methods of forming absorbent pads. These advantages relate both to the lower cost of the instant invention as well as the better performance achieved in an absorbent pad such as in the instant invention. The pad of the instant invention is better in performance in that the inner body-side liner is in contact with the absorbent material and therefore the liquid is better transported through the impervious liner onto the absorbent material. Further, the absorbent material may be a coform that has been formed upon the permeable pad liner, thereby allowing the permeable liner to serve both as the liner for the pad and also the carrier sheet for the coform web during formation. The use of the extrusion-coated spunbonded hydrophobic fabric on the surface of the impermeable sheet eliminates the wicking leakage of the material while the hydrophilic liner material aids in transferring of liquids such as urine to the absorbent coform material. These and other advantages of the invention will be obvious from the detailed description of the drawings and discussion below. The use of one spunbonded fabric as both the carrier for coform formation and the permeable body-side liner is a cost savings.

Figure 1:
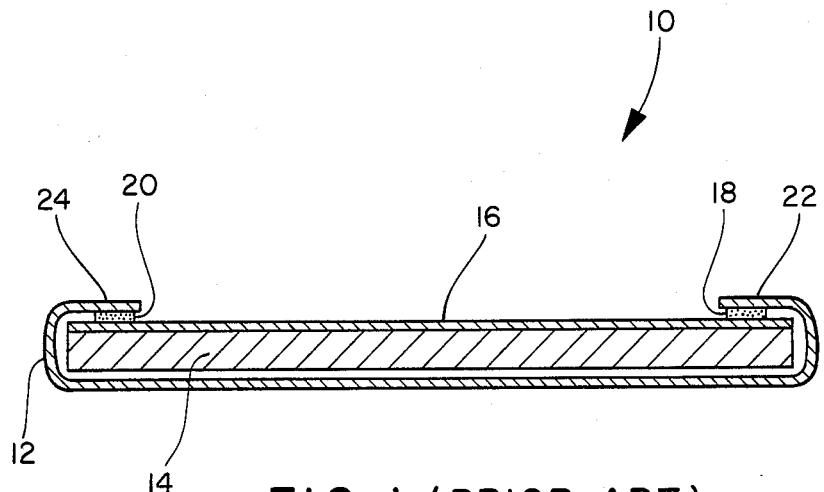
FIGS. 1, 2, and 3 are cross-sectional illustrations of prior art absorbent pads.
Figure 2:
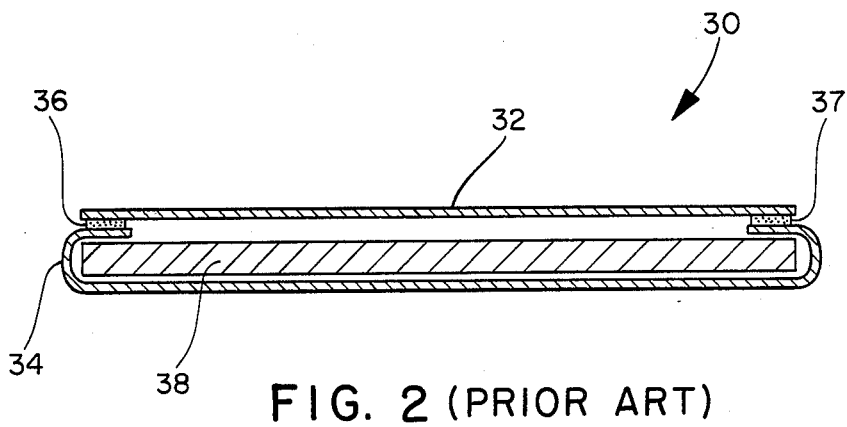

FIG. 1 is an illustration of a prior art structure in absorbent pads generally indicated as 10 in which an impervious covering 12 is wrapped over the absorbent material 14 and adhered to the pervious liner material 16 by glue at 18 and 20. This structure has the disadvantage that when in use the polymer in areas 22 and 24 may be an irritant to the wearer as it tends to cause perspiration and reddening of the skin. The pervious liner also is not adhered to the absorbent material and liquid may run on its surface rather than pass through to the absorbent material. The structure of FIG. 2 also is a prior art structure in which the pad generally indicated as 30 is composed of a pervious liner 32 on the body side of the pad. An impervious liner 34 is fastened to the pervious body-side liner 32 at glue lines 36 and 37. The inner absorbent material is indicated as 38. This construction has the disadvantage that the liner material 32 may wick body fluids to the outside of the pad 30. Further, it has the disadvantage that the pervious member 32 is not in contact with the absorbent 38 and therefore fluids may run along the liner 32 and cause leakage rather than being absorbed by the absorbent 38.

Figure 3:
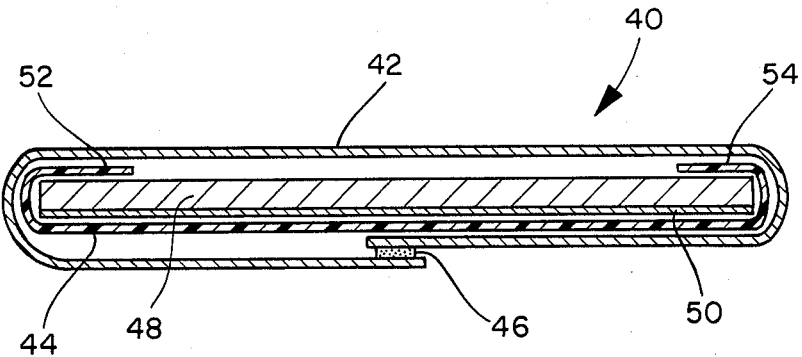

FIG. 3 is an illustration in cross-section of a prior art commercially available incontinent care pad construction in which the pad 40 is wrapped with pervious material 42. The pervious layer 42 completely surrounds the impermeable sheet member 44 and is sealed on the side away from the body at 46. The absorbent material 48 has a pervious backing member 50 which served as a base sheet during formation. The pervious backing member 48 is a coform material that has been above described as an airformed blend of wood fibers and meltblown polymer, preferably polypropylene. This pad while effective does have the disadvantage that the permeable member 42 is generally hydrophobic to inhibit wicking of moisture around the baffle structures 52 and 54. Since it is hydrophobic, liquids such as urine will tend to run along the surface rather than passing through unless the impervious liner 42 is directly in contact with the coform absorbent 48. Also as is readily apparent, this device utilizes more material than is actually necessary in efficiently performing its function. There is extra wrapping material 42 and further a layer 50 on which the coform is formed that also is nonfunctional in the article, although is functional during formation of the coform on the foraminous belt. Coform formation is disclosed in U.S. Pat. No. 4,100,324 of Anderson herein incorporated by reference.

Figure 4:
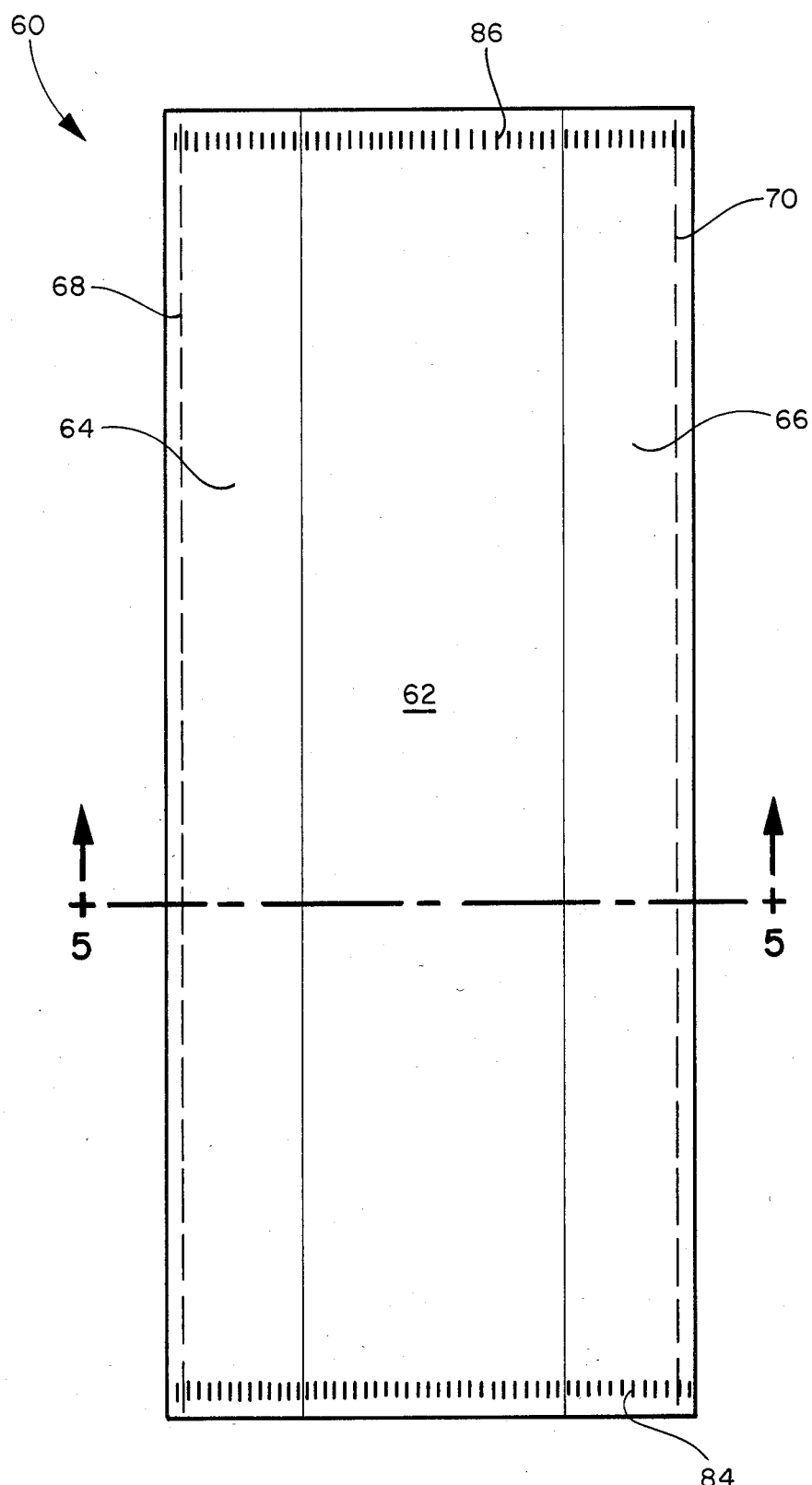
FIG. 4 is a plan view of the pad in accordance with the invention.
Figure 5:
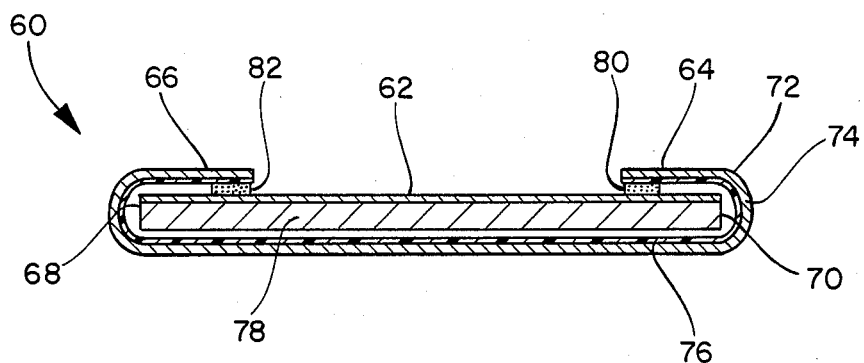
FIG. 5 is a cross-section of the pad of FIG. 4 on cross-sectional line 5—5.

FIG. 4 is a plan view of the baffle pad 60 in accordance with the invention. The pad 60 is formed with a pervious liner 62 and baffle members 64 and 66 extending upwards on each side. The absorbent member extends substantially to the long edges of the pad 68 and 70 beneath baffle 64 and 66. In FIG. 5, which is a cross-section taken cross-sectional line 5—5 of FIG. 4, the structure of the invention is shown with the outer impervious member 72 being composed of two layers. One layer is a fabric 74, preferably a hydrophobic spunbonded polymer, and the second layer an impervious layer 76, composed of the impermeable polymer 76 that is preferably connected with fabric layer 74 during extrusion and forms a very thin, strong and pleasant-feeling composite member that is impermeable as well as being more comfortable for the wearer. In baffle sections 64 and 66 the impermeable member is exposed to the body of the wearer and the fabric contacting the skin is more comfortable. The pad preferably is formed of a coform absorbent 78 that is formed on the permeable cover 62. The cover 62 is preferably a hydrophilic permeable fabric that will aid in passing of liquids such as urine through the permeable surface to the absorbent 78. The baffles 66 and 64 are fastened to the liner 62 by glue areas 80 and 82. The use of hot-melt adhesives in construction of incontinent garments and diapers is well know. It is also possible that this seal might be accomplished by ultrasonics. As illustrated in FIG. 4, the end bond lines 84 and 86 are formed by ultrasonic sealing of the pad at the ends. However, the end seals also could be formed by gluing. While illustrated with the absorbent 78 extending to the end of the pad 60, it is possible to end the absorbent short of the end seals 84 and 86 and seal the liner 62 directly to the impervious layer 72.

Figure 6:
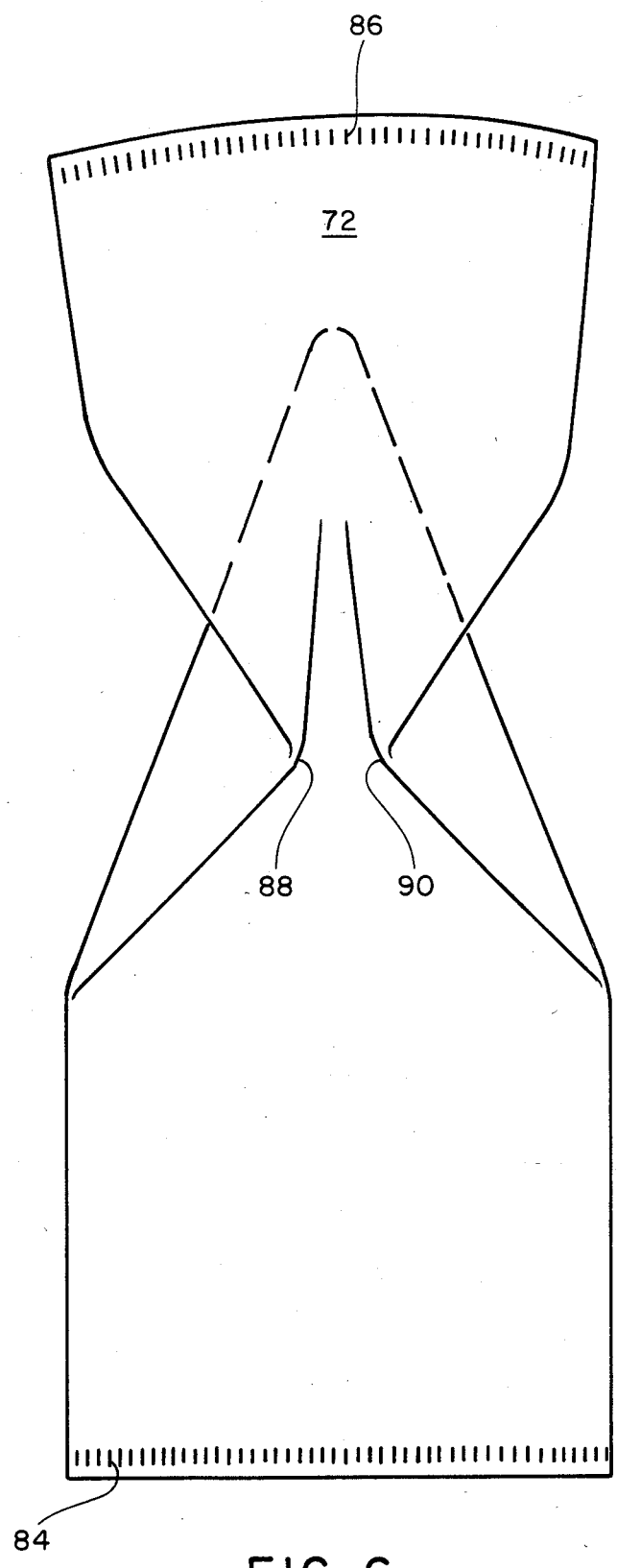
FIG. 6 is a view of an incontinent garment pad folded and with the impervious liner toward the viewer.
Figure 7:
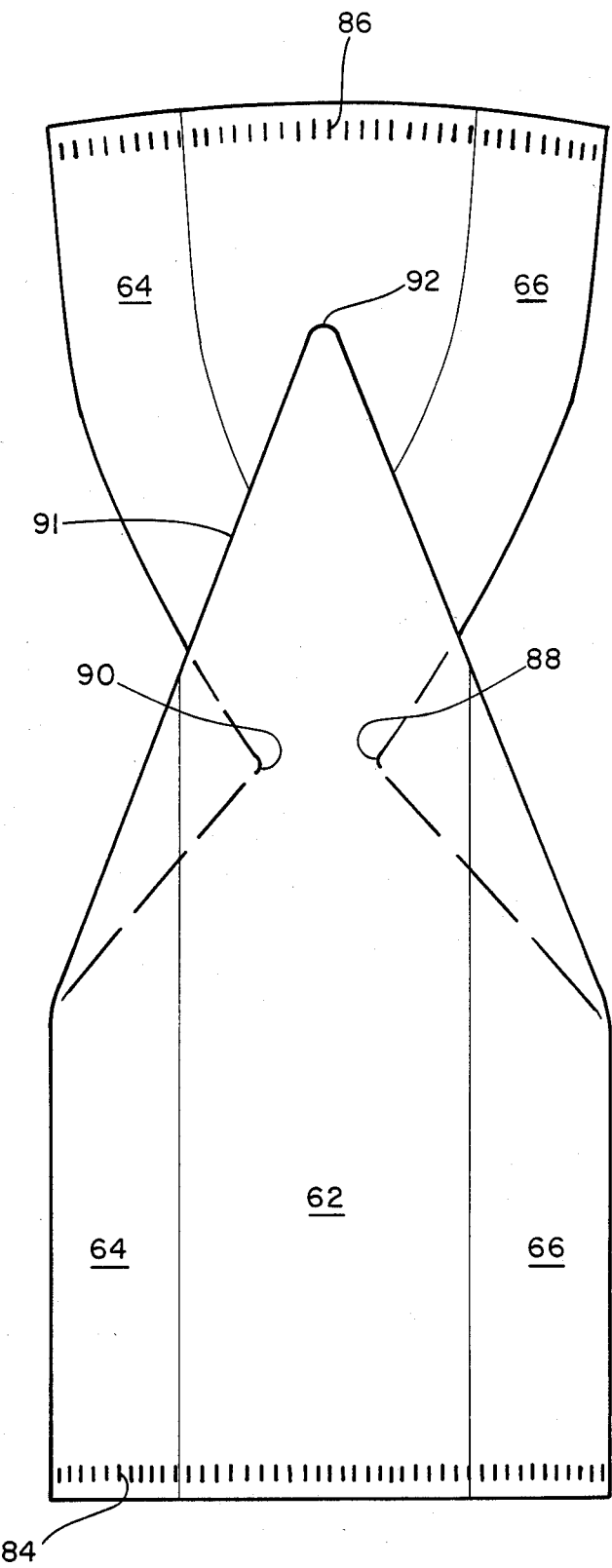
FIG. 7 is the pad of FIG. 6, viewed from the body side.

FIGS. 6 and 7 illustrate a folded pad. This pad is folded in accordance with the description in U.S. Pat. No. 4,1182,334—Johnson. The pad is viewed in FIG. 6 from the impervious liner side and in FIG. 7 from the body side. The folds are the result of the garment being tacked at points 88 and 90 on the impervious liner side. This results in a V-shaped structure 91 forming a pocket at 92 at the point of the V. The fold leaves a large amount of baffle 64 and 66 exposed to the body side. In the instant invention this is covered with the spunbonded fabric that forms the surface of the impervious member 72 such that it does not irritate the wearer. Further, the spunbonded material of the impervious member is hydrophobic and does not tend to wick urine around the edge of the device to wet the garments of the wearer. The pervious member 62 being adhered to the coform absorbent material 78 transfers urine very well onto the interior absorbent. The garment as illustrated in FIGS. 6 and 7 is intended to be worn within a tight-fitting undergarment of ordinary design or may be utilized with a special stretchable underpant that will hold the garment in place.

Figure 8:
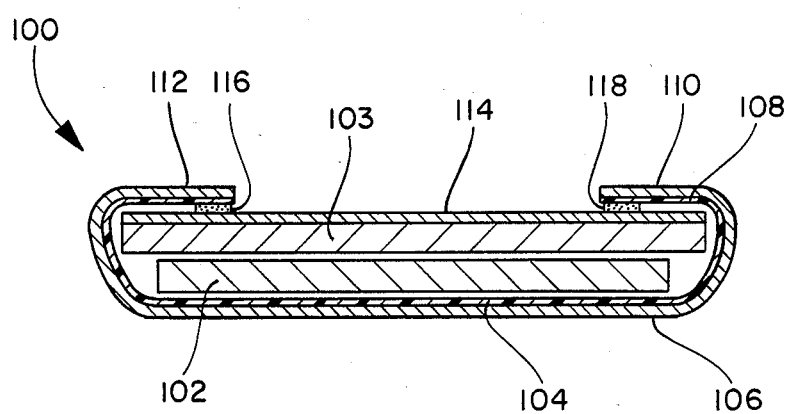
FIG. 8 is a cross section of a pad of the invention having two absorbent layers.

There is illustrated in FIG. 8 an alternative embodiment of a pad in accordance with in the invention. This structure is a preferred structure for some incontinent garments. The alternate embodiment differs from the embodiment as shown in the cross-section of FIG. 5 in that there are two absorbent layers. The garment 100 has two absorbent layers, 102 and 103. These layers are surrounded by an impermeable layer 104 comprised of a surface layer 106 of a fabric and an inner layer 10 formed of a polymer. The impermeable outer covering is wrapped to form a baffle at 110 and 112, and adhered to the permeable cover sheet 114 by glued areas 116 and 118. The formation of a two-layer structure has the advantage that the absorbency may be increased in target areas by forming a double layer only at that section. Further, it is possible that the layer 102 that is further from the wearer may have superabsorbent in it. Generally, the superabsorbent is not placed against the body of the wearer as it has a slimy feel and also may be an irritant. It is also possible in some instances that a sheet of superabsorbent will be placed between the two layers of absorbent material.

While the invention has been illustrated with specific absorbent pad structure suitable for incontinent garments, as above stated the pads formed according to the invention if properly sized would also be usable as catamenial pads, bandages, diapers or other absorbent dressings. Further, the devices of the invention may have various fastening or suspension systems to hold them in place. Further they may be provided with adhesive tabs for fastening or strips of adhesive on the outside for adhesion to undergarments. The pads also may be shaped and have elastic to form shapes that conform to the body.

The impermeable covering material for the garment of the invention is formed by extrusion of a layer of polymer onto a fabric material. The fabric is preferably a hydrophobic material or a fabric that has been treated to render it hydrophobic. The polymer material is preferably a polyethylene or polypropylene polymer or copolymer. The fabric may be any low-cost fabric that has good adhesion properties to the molten polymer and will not melt at the molten polymer temperature. A preferred material is spunbonded polypropylene or polyethylene fibers as these materials are low in cost and a very thin layer will add strength to the polymer film, allowing a thinner polymer film to be used without deterioration of resistance to pinholing or tearing. The preferred impermeable layer consists of 0.5 to 1.0 mil polypropylene polymer film adhered to spunbonded polypropylene fabric sheet of 10 to 25 grams per square meter.

The absorbent layer having an integral surface of a permeable layer may be any desired absorbent material. Typical such materials are wood fibers, referred to as fluff. A preferred material is the material commonly referred to as coform that is an air-laid blend of cellulose fibers and meltblown polypropylene. The formation of this blend as above stated is disclosed in U.S. Pat. No. 4,100,324—Anderson et al. Such material has found use in wipes and as absorbent materials for feminine care and incontinent products. It is also within the invention that the bonded meltblown and the wood fibers could have additives such as superabsorbents or clay material, as is disclosed in British patent application publication No. 2,113,731 of Aug. 10, 1983. It is also possible that the absorbent could be a meltblown with synthetic staple fibers added or without additional staple fibers but with the addition of a superabsorbent such as disclosed in U.S. Pat. No. 4,429,001—Koplin et al. The formation of meltblown material is accomplished by air forming onto a forming belt which is a foraminous member through which the air utilized in the meltblowing process is extracted. The foraminous belt generally carries a forming layer on which the meltblown material is laid. This layer may be a spunbonded material and in that case there is some bonding between the meltblown material and the spunbonded substrate. Use of a spun-bond forming layer is preferred for the absorbent's permeable cover member in the pad of the instant invention as it is lower in cost. However, it is possible that the permeable cover member of the invention pads could be later attached to the absorbent material, although such an assembly step would necessarily raise the cost. The cover could be attached to the absorbent layer by adhesives, ultrasonics, heat or embossing. The separate attachment of the pervious liner would be particularly desirable if the end seals 84 and 86 are to connect the liner 62 and impervious cover 72 and the absorbent does not extend to the area of the end seals.

The permeable body-side cover material may be any material that allows penetration of liquids. Typical of such materials are perforated plastic sheets, tissue and woven fabrics. A preferred material is meltblown spunbonded polypropylene as it is low in cost, comfortable and stable.

In the invention the permeable body-side liner is treated if necessary to render it hydrophilic. The necessity of treatment will depend on the chemical properties of the permeable material and whether the material is wetted by water or urine. The spunbonded polypropylene material generally should be treated by a wetting agent or surfactant such as Triton X-102 (Trademark) of Rohm & Haas or Aerosol O.T. (Trademark) of American Cyanamid. Triton X-102 is a tertiary-octyl-phenol-poly (ethylene oxide)$_{12-13}$ and Aerosol-OT is a dioctyl-sodium-sulfo-succinate. This surfactant treatment normally would be carried out at the time of formation of the spunbonded material. Spunbonded material may be formed by any conventional process such as that of U.S. Pat. Nos. 3,341,394 and 3,338,992 to Kinney and U.S. Pat. No. 3,692,618 to Dorschner et al. The article of U.S. Pat. No. 3,692,618 of Dorschner at al., when the fibers are bonded by the process of U.S. Pat. No. 3,855,046 to Hanson et al. as the liner formation process is as described in U.S. Pat. No. 3,880,942 of Bernardin, is a suitable liner product as the fibers are laid down in a continuous uniform nonwoven web of suitable strength and permeability for use as a liner material.

I claim:

1. A rectangular absorbent pad comprising an impervious outer layer comprising a polymer sheet integrally adhered to a fabric and oriented such that fabric is on the exterior of said pad, an inner absorbent member, and a pervious body-side liner adhered to the body side of said absorbent member wherein said impervious outer layer overlaps the long edges of said absorbent member and is adhered to said pervious liner on the body side of said pad.

2. The pad of claim 1 wherein said liner is hydrophilic.

3. The pad of claim 1 wherein the exterior fabric is hydrophobic.

4. The pad of claim 1 wherein said fabric is a spunbonded fabric.

5. The pad of claim 1 wherein said pervious liner is a spunbonded material.

6. The pad of claim 1 wherein said absorbent member is a coform material.

7. The pad of claim 1 wherein said pervious liner served as the forming layer for the coform absorbent member.

8. The pad of claim 1 wherein said pad is an incontinent care garment.

9. The pad of claim 1 wherein said pad is a catamenial device.

10. The pad of claim 1 wherein said pad is a diaper.

11. A method of forming a pad comprising providing a permeable rectangular sheet, adhering a rectangular absorbent member to said sheet, placing the absorbent member having said permeable sheet adhered thereto onto a rectangular covering wider in its smaller dimension than the smaller dimension of said absorbent member, folding the long edges of said covering over the long edges of said absorbent and adhering said edges to said permeable sheet, wherein said covering comprises an impermeable composite of fabric and polymer.

12. The method of claim 11 further comprising sealing the narrow ends of the rectangular members together.

13. The method claim 11 wherein said rectangular absorbent member is shorter in its long dimension than said covering and is centered on said permeable sheet.

* * * * *

UNITED STATES PATENT AND TRADEMARK OFFICE
CERTIFICATE OF CORRECTION

PATENT NO. : 4,578,066
DATED : March 25, 1986
INVENTOR(S) : O'Connor

It is certified that error appears in the above-identified patent and that said Letters Patent are hereby corrected as shown below:

Column 4, Line 6, "4,1182,334" should read "4,182,334".

Signed and Sealed this

Seventh Day of April, 1987

Attest:

DONALD J. QUIGG

*Attesting Officer*    *Commissioner of Patents and Trademarks*